United States Patent [19]

Malamas

[11] Patent Number: 5,169,948
[45] Date of Patent: Dec. 8, 1992

[54] PROCESS AND INTERMEDIATES FOR THE PREPARATION OF SPIRO[ISOQUINOLINE-4(1H),3-PYRROLIDINE]1,2,3,5 (2H)-TETRONES WHICH ARE USEFUL AS ALDOSE REDUCTASE INHIBITORS

[75] Inventor: Michael S. Malamas, Jamison, Pa.

[73] Assignee: American Home Products Corporation, New York, N.Y.

[21] Appl. No.: 816,198

[22] Filed: Jan. 2, 1992

Related U.S. Application Data

[62] Division of Ser. No. 703,969, May 22, 1991, Pat. No. 5,106,978.

[51] Int. Cl.$^5$ .................. C07D 217/24; C07D 217/26
[52] U.S. Cl. .................. 546/142; 546/145; 546/146
[58] Field of Search .................. 546/142, 145, 146

[56] References Cited

U.S. PATENT DOCUMENTS 3,948,898  4/1976  Kutter et al. .................. 546/142
4,927,831  5/1991  Malamas .................. 546/18

FOREIGN PATENT DOCUMENTS 0365324  4/1990  European Pat. Off. .
64-135771 5/1989  Japan .................. 546/142

Primary Examiner—C. Warren Ivy
Assistant Examiner—Ba K. Trinh
Attorney, Agent, or Firm—Walter Patton

[57] ABSTRACT

This invention relates to a process for producing spiro-isoquinolinepyrrolidines. The compounds have pharmaceutical properties which render them beneficial for the prevention or treatment of diabetes mellitus associated complications.

1 Claim, No Drawings

PROCESS AND INTERMEDIATES FOR THE PREPARATION OF SPIRO[ISOQUINOLINE-4(1H),3-PYRROLIDINE]1,2,3,5 (2H)-TETRONES WHICH ARE USEFUL AS ALDOSE REDUCTASE INHIBITORS

This is a division of application Ser. No. 07/703,969 filed May 22, 1991, now U.S. Pat. No. 5,106,978.

BACKGROUND OF THE INVENTION

This invention discloses an improved process and for chemical intermediates useful for the synthesis of the spiro[isoquinoline-4(1H),3'-pyrrolidine]-1,2',3,5'(2H)-tetrones represented by formula I:

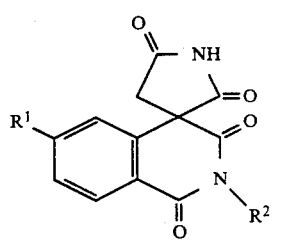

wherein:
$R^1$ is hydrogen, halogen and $R^2$ is dihalogen substituted benzyl or methyl.

PRIOR ART

U.S. Pat. No. 4,927,831, May 22, 1990 discloses the spiro[isoquinoline-4(1H),3'-pyrrolidine]-1,2',3,5'(2H)-tetrones of formula I and their use as aldose reductase inhibitors.

SUMMARY OF THE INVENTION

The process of the present invention is illustrated by the following process:

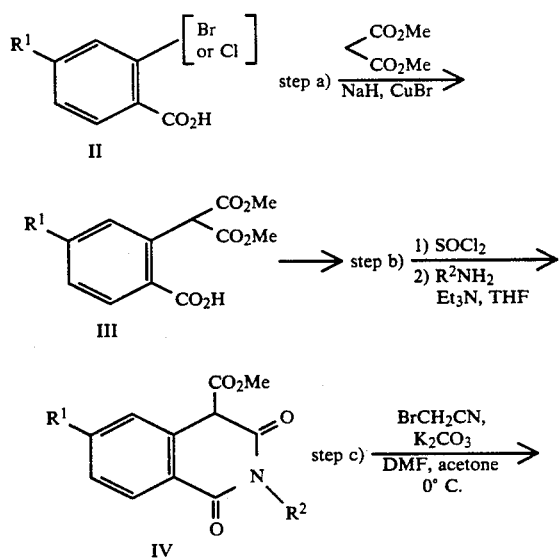

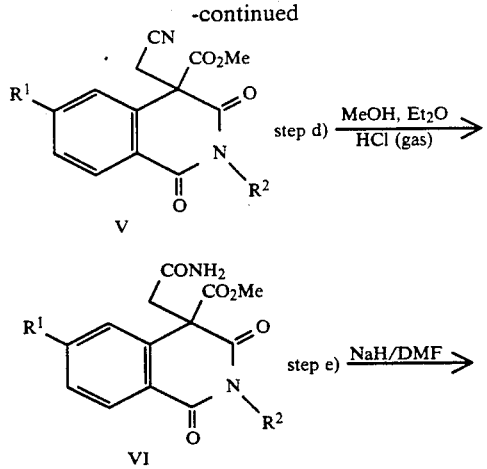

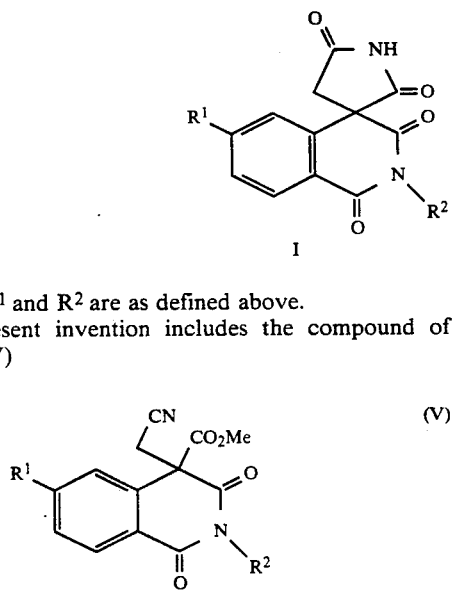

wherein $R^1$ and $R^2$ are as defined above.

The present invention includes the compound of formula (V)

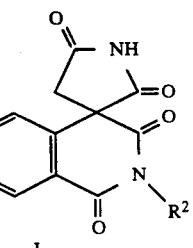

wherein $R^1$ and $R^2$ are as defined above.

(V) is useful as an intermediate for preparing spiro[isoquinoline]-4(1H),3'-pyrrolidine]-1,2',3,5'(2H)-tetrones of formula (I) which have strong aldose reductase inhibiting activity and are expected useful as remedies for diabetic complications.

The following examples further illustrate this invention.

EXAMPLE 1

2-[(4-Bromo-2-fluorophenyl)methyl]-6-fluorospiro[isoquinoline-4(1H),3'-pyrrolidine]-1,2',3,5'(2H)-tetrone

Step a)

2-Carboxy-6-fluorophenyl)propanedioic Acid Dimethyl Ester

To a rapidly stirred cold suspension (0° C.) of 2-chloro-4-fluorobenzoic acid (20.0 g, 114.6 mmol), cuprous bromide (1.64 g, 11.46 mmol) and dimethyl malonate (250 g) was added NaH (80% in mineral oil, 8.25 g, 275.04 mmol) over a 30 minute period, while a stream of dry $N_2$ was passed over the mixture. After the addition of the NaH had been completed, the mixture was stirred at 85° C. for 3 hours. At this point, the suspension had turned to a solid mass, which was dissolved in H$_2$O (1000 mL). The aqueous layer was extracted with diethyl ether (3×500 mL) and was acidified with HCl (2N). The mixture was extracted with EtOAc and dried over MgSO$_4$. Evaporation gave an off-white solid which was recrystallized from ether/hexane (after cooling to −20° C.) to give a white solid (27.5 g, 89%). $^1$H NMR (DMSO-d$_6$, 400 MHz): δ3.68 [s, 6H, (—CO$_2$Me)$_2$], 5.79 (s, 1H, Ar—H), 7.12 (dd, J=10.06 Hz, 2.61 Hz, 1H, Ar—H), 7.33 (dt, J=8.48 Hz, 2.64 Hz, 1H, Ar—H), 8.03 (dd, 8.77 Hz, 6.17 Hz, 1H, Ar—H); IR (KBr, cm$^{-1}$): 3400–2700 (CO$_2$H), 1730 (CO), 1680 (CO); MS (m/e): 270 (M+)—CH$_3$OH), 210 (M+—CH$_3$OH, —CO), 151 (M+—CH$_3$OH—CO—CO$_2$CH$_3$); M.P. 121.5°–123.0° C.

Anal Calc'd: C, 53.34; H, 4.10. Found: C, 53.36; H, 3.93.

The following compounds were prepared in substantially the same manner as that of Example 1 Step a):

2-Carboxyphenyl)propanedioic Acid Dimethyl Ester $^1$H NMR (DMSO-d$_6$, 400 MHz): δ3.67 [s, 6H, —CH(C)$_2$CH$_3$)$_2$], 5.72 [s, 1H, —CH(CO$_2$CH$_3$)$_2$], 7.3 (d, J=7.76 Hz, 1H, Ar—H), 7.45 (dt, J=7.66 Hz, 1.12 Hz, 1H, Ar—H), 7.6 (dt, J=7.66 Hz, 1.45 Hz, 1H, Ar—H), 7.94 (dd, J=7.8 Hz, 1.33 Hz, 1H, Ar—H), 13.2 (s, 1H, —CO$_2$H); IR (KBr, cm$^{-1}$): 3300–2700 (CO$_2$H), 1750 (CO), 1730 (CO), 1680 (CO); MS (m/e): 252 (M+), 220 (M+—CH$_3$OH), 188 (M+—2×CH$_3$OH); M.P. 119°–120° C.

Anal. Calc'd: C, 57.14; H, 4.80. Found: C, 57.05; H, 4.78.

2-Carboxy-6-chlorophenyl)propanedioic Acid Dimethyl Ester $^1$H NMR (DMSO-d$_6$, 200 MHz): δ3.69 [s, 6H, (—CO$_2$Me)$_2$], 5.78 [s, 1H, Ar—CH(CO$_2$Me)$_2$], 7.38 (d, J=1.8 Hz, 1H, Ar—H), 7.58 (dd, J=7.8 Hz, 1.8 Hz, 1H, Ar—H), 7.96 (d, J=8.2 Hz, 1H, Ar—H), 13.5 (br s, 1H, —CO$_2$H); IR (KBr, cm$^{-1}$): 3200–2700 (CO$_2$H), 1760 (CO), 1740 (CO), 1690 (CO); MS (m/e): 286 (20M+), 254 (64, M+—CH$_3$OH), 222 (60, M+2×CH$_3$OH)

Anal. Calc'd: C, 50.28; H, 3.87. Found: C, 50.40; H, 3.87.

Step b)

2-[(4-Bromo-2-fluorophenyl)methyl-6-fluoro-1,2,3,4-tetrahydro-1,3-dioxo-4-isoquinolinecarboxylic Acid Methyl Ester A mixture of (2-carboxy-6-fluorophenyl)propanedioic acid dimethyl ester (6.0 g, 22.22 mmol) and SOCl$_2$ (50 mL) was refluxed for 1 hour. The volatiles were removed in vacuo and the acid chloride was dissolved in THF (20 mL). In a second flask were placed 4-bromo-2-fluorobenzylamine (4.98 g, 24.44 mmol), triethylamine (15.48 mL, 111.1 mmol) and THF (150 mL). The contents of the first flask were added to the second flask and the mixture was stirred for 20 minutes. The formed suspension was poured into H$_2$O (1500 mL), stirred for 10 minutes and acidified with HCl (2N). The mixture was extracted with EtOAc and the organic layer was dried over MgSO$_4$. Evaporation gave a yellowish solid which was recrystallized from acetone/ether/hexane (after cooling −20° C.) to give a white solid (7.85 g, 83%). $^1$H NMR (DMSO-d$_6$, 400 MHz): δ3.98 (s, 3H, —CO$_2$CH$_3$), 5.27 (s, 2H, —NCH$_2$—), 7.08 (t, J=7.95 Hz, 2H, Ar—H), 7.2 (m, 1H, Ar—H), 7.34 (m, 2H, Ar—H, —OH), 7.54 (m, 1H, Ar—H), 8.1–8.26 (m, 2H, Ar—H); IR (KBr, cm$^{-1}$): 1680 (CO), 1660 (CO), 1610 (CO); MS (m/e): 423 (M+), 391 (M+—CH$_3$OH); M.P. 157°–158° C.

Anal. Calc'd: C, 50.97; H, 2.85; N, 3.30. Found: C, 50.86; H, 2.86; N, 3.33.

The following compounds were prepared in substantially the same manner as that of Example 1 Step b):

2-[(4-Bromo-2-fluorophenyl)methyl]-1,2,3,4-tetrahydro-1,3-dioxo-4-isoquinolinecarboxylic Acid Methyl Ester $^1$H NMR (DMSO-d$_6$, 400 MHz): δ[3.67, 3.99 (s, 3H, —CO$_2$CH$_3$, tautomeric], [5.06 (q, J=15.4 Hz), 5.29 (s) 2H, N—CH$_2$—, tautomeric], 5.03 (s, 1H, —CH CO$_2$CH$_3$, tautomeric), 7.07–8.44 (m, 7H, Ar—H, tautomeric); IR (KBr, cm$^{-1}$): 1675 (CO), 1610 (CO), 1490 795 (m); MS (m/e): 405 (M+), 373 (M+—MeOH); M.P. 149°–150° C.

Anal. Calc'd: C, 53.22; H, 3.23; N, 3.45. Found: C, 52.91; H, 3.20; N, 3.27.

6-Chloro-1,2,3,4-tetrahydro-2-methyl-1,3-dioxo-4-isoquinolinecarboxylic Acid Methyl Ester $^1$H NMR (DMSO-d$_6$, 200 MHz): δ[3.23 (s), 3.44 (s), tautomeric, 3H, —NCH$_3$], [3.71 (s), 4.03 (s), tautomeric, 3H, —CO$_2$CH$_3$], 7.3–8.4 (tautomeric, Ar—H, —OH, 4H); IR (KBr, cm$^{-1}$): 3440 (OH), 1680 (CO), 1600 (CO); MS (m/e): 267 (M+), 235 (M+—OMe); M.P. 166°–167° C.

Anal. Calc'd: C, 53.85; H, 3.77; N, 5.23. Found: C, 53.66; H, 3.63; N, 5.14.

1,2,3,4-Tetrahydro-2-methyl-1,3-dioxo-4-isoquinolinecarboxylic Acid Methyl Ester $^1$H NMR (DMSO-d$_6$, 200 MHz): δ[3.24 (s), 3.46 (s), tautomeric, 3H, —NCH$_3$], [3.7 (s), 4.03 (s), tautomeric, 3H, —CO$_2$CH$_3$], 7.4–8.45 (tautomeric, 4H, Ar—H); IR (KBr, cm$^{-1}$): 3400 (OH), 1670 (CO), 1600 (CO); MS (m/e): 233 (M+), 118 (M+—CO$_2$Me, —CONCH$_3$); M.P. 130°–131° C.

Anal. Calc'd: C, 61.80; H, 4.75; N, 6.01. Found: C, 61.62; H, 4.89; N, 5.92.

Step c)

2-[(4-Bromo-2-fluorophenyl)methyl]-4-cyanomethyl-6-fluoro-1,2,3,4-tetrahydro-1,3-dioxo-4-isoquinolinecarboxylic Acid Methyl Ester To a cold (0° C.) suspension of 2-[(4-bromo-2-fluorophenyl)methyl]-6-fluoro-1,2,3,4-tetrahydro-1,3-dioxo-4-isoquinolinecarboxylic acid methyl ester (11.0 g, 25.94 mmol), K$_2$CO$_3$ (3.58 g, 25.94 mmol), DMF (50 mL) and acetone (50 mL) was added freshly distilled BrCH$_2$CN (3.61 mL, 51.88 mmol) and the mixture was stirred for 10 hours at 0° C. and kept in the refrigerator for 4 days. The mixture was then poured into H$_2$O, acidified with HCl (2N), and extracted with EtOAc. The organic extracts were dried over MgSO$_4$. Evaporation and purification by flash chromatography hexane/EtOAc (5/1) gave a light yellow solid (11.45 g, 95.4%). $^1$H NMR (DMSO-d$_6$, 300 MHz): δ3.63 (s, 3H, —CO$_2$CH$_3$), 3.73 (d, J=16.8 Hz, 1H, —HCHCN), 3.9 (d, J=16.8 Hz, 1H, —HCHCN), 5.14 (dd, J=15.2 Hz, 2H, —NCH$_2$—), 7.16 (t, J=8.1 Hz, 1H, Ar—H), 7.36 (dd, J=8.1 Hz, 1.8 Hz, 1H, Ar—H), 7.57 (m, 2H, Ar—H), 7.64 (dd, J=9.3 Hz, 2.4 Hz, 1H, Ar—H), 8.3 (dd, J=8.7 Hz, 5.7 Hz, 1H, Ar—H); IR (KBr, cm$^{-1}$): 2250 (CN), 1760 (CO), 1720

(CO), 1675 (CO); MS (m/e): 463 (M+H)+; M.P. 127°-128° C.

Anal. Calc'd: C, 51.86; H, 2.83; N, 6.05, Found: C, 51.73; H, 3.00; N, 5.96.

The following compounds were prepared in substantially the same manner as that of Example 2, Step c).

2-[(4-Bromo-2-fluorophenyl)methyl]-4-cyanomethyl-1,2,3,4-tetrahydro-1,3-dioxo-4-isoquinolinecarboxylic Acid Methyl Ester $^1$H NMR (DMSO-$d_6$, 400 MHz): δ3.61 (s, 3H, —CO$_2$CH$_3$), 3.72 (d, J=17.0 Hz, 1H, —HCHCN), 3.88 (d, J=17.0 Hz, 1H, —HCHCN), 5.14 (dd, J=15.2 Hz, 2H, —NCH$_2$—), 7.17 (t, J=8.3 Hz, 1H, Ar—H), 7.39 (dd, J=8.3 Hz, 1.87 Hz, 1H, Ar—H), 7.55 (dd, J=9.7 Hz, 2.1 Hz, 1H, Ar—H), 7.68 (m,2H, Ar—H), 7.86 (dt, J=7.7 Hz, 1.45 Hz, 1H, Ar—H), 8.21 (dd, J=7.64 Hz, 1.25 Hz, 1H, Ar—H); IR (KBr, cm$^{-1}$): 2240 (CN), 1760 (CO), 1720 (CO), 1680 (CO); MS (m/e): 444 (M+), 404 (M+—CH$_2$CN); M.P. 108°-110° C.

Anal. Calc'd: C, 53.94; H, 3.15; N, 6.29, Found: C, 53.94; H, 3.38; N, 5.93.

4-Cyanomethyl-2-methyl-1,2,3,4-tetrahydro-1,3-dioxo-4-isoquinolinecarboxylic Acid Methyl Ester $^1$H NMR (DMSO-$d_6$, 400 MHz): δ3.31 (s, 3H, —NCH$_3$), 3.65 (s, 3H, —CO$_2$CH$_3$), 3.67 (d, J=17.0 Hz, 1H, —HCHCN), 3.76 (d, J=17.0 Hz, 1H, —HCHCN), 7.58 (dd, J=7.9 Hz, 1.04 Hz, 1H, Ar—H), 7.69 (dt, J=7.9 Hz, 1.04 Hz, 1H, Ar—H), 7.84 (dt, J=7.26 Hz, 1.45 Hz, 1H, Ar—H), 8.2 (dd, J=7.3 Hz, 1.45 Hz, 1H, Ar—H); IR (KBr, cm$^{-1}$): 2250 (CN), 1760 (CO), 1730 (CO), 1670 (CO); MS (m/e): 272 (M+), 213 (M+—CO$_2$CH$_3$); M.P. 120°-122° C.

Anal. Calc'd: C, 61.76; H, 4.44; N, 10.29, Found: C, 61.72; H, 4.57; N, 10.07.

6-Chloro-4-cyanomethyl-2-methyl-1,2,3,4-tetrahydro-1,3-dioxo-4-isoquinolinecarboxylic Acid Methyl Ester $^1$H NMR (DMSO-$d_6$, 400 MHz): δ3.3 (s, 3H, —NCH$_3$), 3.67 (s, 3H, —CO$_2$CH$_3$), 3.74 (d, J=17.0 Hz, 1H, —HCHCN), 3.87 (d, J=17.0 Hz, 1H, —HCHCN), 7.7 (m, 2H, Ar—H), 8.2 (d, J=9.1 Hz, 1H, Ar—H); IR (KBr, cm$^{-1}$): 2250 (CN), 1770 (CO), 1720 (CO), 1675 (CO); MS (m/e): 306 (M+), 247 (M+—CO$_2$CH$_3$); M.P. 130°-132° C.

Anal. Calc'd: C, 54.83; H, 3.62; N, 9.13, Found: C, 54.74; H, 3.74; N, 8.89.

Step d)

4-(2-Amino-2-oxoethyl)-2-[(4-bromo-2-fluorophenyl)methyl]-6-fluoro-1,2,3,4-tetrahydro-1,3-dioxo-4-isoquinolinecarboxylic Acid Methyl Ester.

Dry HCl gas was passed through a cold (0° C.) suspension of 2-[(4-bromo-2-fluorophenyl)methyl]-4-cyanomethyl-6-fluoro-1,2,3,4-tetrahydro-1,3-dioxo-4-isoquinolinecarboxylic acid methyl ester (7.7 g, 16.63 mmol) in dimethyl ether (300 mL) and anhydrous MeOH (2.02 mL, 49.89 mmol). The suspension during the introduction of the HCl gas turned into a solution. The mixture was kept at room temperature for 4.5 days and then hexane (500 mL) was added. Most of the volatiles were removed in vacuo to the point that a white solid started to precipitate, and the mixture was cooled to 0° C. for 5 hours. The precipitated solid was filtered, washed with hexane and dried to yield a white solid (7.56 g, 95%). $^1$H NMR (DMSO-$d_6$, 400 MHz): δ3.49 (d, J=16.65 Hz, 1H, —CH$_2$CONH$_2$), 3.56 (s, 3H, —CO$_2$CH$_3$), 3.59 (d, J=16.65 Hz, 1H, —CH$_2$CONH$_2$), 5.08 (dd, J=15.48 Hz, 2H, —NCH$_2$), 6.94 (s, 1H, —CONH$_2$), 7.21 (t, J=8.22 Hz, 1H, Ar—H), 7.30 (dd, J=8.27 Hz, 1.64 Hz, 1H, Ar—H), 7.38-7.46 (m, 2H, Ar—H), 7.51 (s, 1H, —CONH$_2$), 7.54 (dd, J=9.81 Hz, 1.83 Hz, 1H, Ar—H), 8.20 (dd, J=8.74 Hz, 5.84 Hz, 1H, Ar—H); IR (KBr, cm$^{-1}$): 3440 (NH), 3350 (NH), 1740 (CO), 1710 (CO), 1670 (CO), 1660 (CO); MS (m/e): 481 (M+H)+; M.P. 202°-204° C.

Anal. Calc'd: C, 49.92; H, 3.14; N, 5.82, Found: C, 49.79; H, 3.36; N, 5.51.

The following compounds were obtained in substantially the same manner as that of Example 1, Step d):

4-(2-Amino-2-oxoethyl)-2-[(4-bromo-2-fluorophenyl)methyl]-1,2,3,4-tetrahydro-1,3-dioxo-4-isoquinolinecarboxylic Acid Methyl Ester $^1$H NMR (DMSO-$d_6$, 400 MHz): δ3.53 (s, 3H, —CO$_2$CH$_3$), 3.51 (q, J=16.6 Hz, 2H, —CH$_2$CONH$_2$), 5.1 (q, J=15.4 Hz, 2H, —NCH$_2$—), 6.88 (s, 1H, —CONH$_2$), 7.23 (t, J=8.0 Hz, 1H, Ar—H), 7.3 (dd, J=8.3 Hz, 1.84 Hz, 1H, Ar—H), 7.46 (d, J=7.98 Hz, 1H, Ar—H), 7.52 (s, 1H, —CONH$_2$), 7.54-7.60 (m, 2H, Ar—H), 7.75 (dt, J=7.76 Hz, 1.39 Hz, 1H, Ar—H), 8.1 (dd, J=7.87 Hz, 1.22 Hz, 1H, Ar—H); IR (KBr, cm$^{-1}$): 3450 (NH), 17340 (CO), 1720 (CO), 1670 (CO); MS (m/e): 462 (M+); M.P. 180°-182° C.

Anal. Calc'd: C, 51.84; H, 3.46; N, 6.05, Found: C, 51.72; H, 3.65; N, 5.91.

4-(2-Amino-2-oxoethyl)-6-chloro-1,2,3,4-tetrahydro-2-methyl-1,3-dioxo-4-isoquinolinecarboxylic Acid Methyl Ester $^1$H NMR (DMSO-$d_6$, 200 MHz): δ3.26 (s, 3H, —NCH$_3$), 3.51 (q, J=17.5 Hz, 2H, —CH$_2$CONH$_2$), 3.59 (s, 3H, —CO$_2$CH$_3$), 6.85 (s, 1H, —CONH$_2$), 7.5 (s, 1H, —CONH$_2$), 7.53 (d, J=2.0 Hz, 1H, Ar—H), 7.62 (dd, J=8.6 Hz, 2.0 Hz, 1H, Ar—H), 8.16 (d, J=8.0 Hz, 1H, Ar—H); IR (KBr, cm$^{-1}$): 3420 (NH), 1760 (CO), 1710 (CO), 1660 (CO); MS (m/e): 325 (M+H)+; M.P. 220°-222° C.

Anal. Calc'd: C, 51.78; H, 4.03; N, 8.63, Found: C, 51.76; H, 4.20; N, 8.32.

4-(2-Amino-2-oxoethyl)-1,2,3,4-tetrahydro-2-methyl-1,3-dioxo-4-isoquinolinecarboxylic Acid Methyl Ester $^1$H NMR (DMSO-$d_6$, 200 MHz): δ3.27 (s, 3H, —NCH$_3$), 3.49 (s, 2H, —CH$_2$CO$_2$H), 3.56 (s, 3H, —CO$_2$CH$_3$), 6.78 (s, 1H, —CONH$_2$), 7.4-7.6 (m, 3H, Ar—H, —CONH$_2$), 7.69 (dt, J=7.6 Hz, 2Hz, 1H, Ar—H), 8.16 (d, J=8.2 Hz, 1H, Ar—H); IR (KBr, cm$^{-1}$): 3420 (NH), 1760 (CO), 1660 (CO); MS (m/e): 291 (M+H)+; M.P. 229°-231° C.

Anal. Calc'd: C, 57.93; H, 4.86; N, 9.65, Found: C, 57.59; H, 4.93; N, 9.49.

Step e)

2-[(4-Bromo-2-fluorophenyl)methyl]-6-fluorospiro[isoquinoline-4(1H),3'-pyrrolidine]-1,2',3,5'(2H)-tetrone To a solution of 4-(2-amino-2-oxoethyl)-2-[(4-bromo-2-fluorophenyl)methyl]-6-fluoro-1,2,3,4-tetrahydro-1,3-dioxo-4-isoquinolinecarboxylic acid methyl ester (6.0 g, 12.47 mmol) in DMF (50 mL) was added portionwise NaH (80% dispersion in oil, 374.2 mg, 12.47 mmol) over a 10 minute period. After stirring for 30 minutes, the mixture was poured into H$_2$O, acidified with HCl (2N)

and extracted with EtOAc. The organic extracts were dried over MgSO$_4$. Evaporation and purification by flash chromatography (hexane/EtOAc 3/1) on acid washed silica gel (5% H$_3$PO$_4$ in MeOH), yielded a white solid (4.3 g, 86%). $^1$H NMR (DMSO-d$_6$, 400 MHz): δ3.44 (s, 2H, CON$\underline{H}$—), 5.05 (s, 2H, —CN$\underline{H_2}$—), 7.14 (t, J=8.42 Hz, 1H, Ar—$\underline{H}$), 7.32 (dd, J=7.58 Hz, 1.26 Hz, 1H, Ar—$\underline{H}$), 7.48 (dt, J=8.64 Hz, 2.1 Hz, 1H, Ar—$\underline{H}$), 7.53 (dd, 9.89 Hz, 1.89 Hz, 1H, Ar—$\underline{H}$), 7.75 (dd, 9.69 Hz, 2.32 Hz, 1H, Ar—$\underline{H}$), 8.22 (dd, J=8.84 Hz, 5.89 Hz, 1H, Ar—$\underline{H}$), 12.0 (s, 1H, —CON$\underline{H}$CO—); IR (KBr, cm$^{-1}$): 3400 (NH), 3260 (NH), 1735 (CO), 1680 (CO); MS (m/e): 449 (M+H)$^+$; M.P. 230°-232° C.

Anal. Calc'd: C, 50.80; H, 2.47; N, 6.24, Found: C, 50.87; H, 2.53; N, 6.08.

The following compounds were prepared in substantially the same manner as that of example 1 step e):

2-[(4-Bromo-2-fluorophenyl)methyl]spiro[isoquinoline-4(1H),3'-pyrrolidine]-1,2',3,5'(2H)-tetrone $^1$H NMR (DMSO-d$_6$, 400 MHz): δ3.47 (J=18.24 Hz, 2H, —C$\underline{H_2}$CONH—), 5.06 (s, 2H, —NC$\underline{H_2}$—), 7.14 (t, J=8.2 Hz, 1H, Ar—$\underline{H}$), 7.33 (dd, J=8.28 Hz, 1.71 Hz, 1H, Ar—$\underline{H}$), 7.55 (dd, J=9.9 Hz, 1.8 Hz, 1H, Ar—$\underline{H}$), 7.62 (t, J=7.6 Hz, 1H, Ar—$\underline{H}$), 7.68 (d, J=7.78 Hz, 1H, Ar—$\underline{H}$), 7.78 (dt, J=8.85 Hz, 1.12 Hz, 1H, Ar—$\underline{H}$), 8.15 (dd, J=7.86 Hz, 1.3 Hz, 1H, Ar—$\underline{H}$), 12.01 (s, 1H, —CON$\underline{H}$CO—); IR (KBr, cm$^{-1}$): 3450 (NH), 3250 (NH), 1730 (CO), 1680 (CO); MS (m/e): 430 (M+), 387 (M+—CONH); M.P. 112°-114° C.

Anal. Calc'd: C, 52.92; H, 2.80; N, 6.50, Found: C, 52.61; H, 2.70; N, 6.46.

6-Chloro-2-methylspiro[isoquinoline-4(1H)3'-pyrrolidine]-1,2',3,5'(2H)-tetrone $^1$H NMR (DMSO-d$_6$, 400 MHz): δ3.22 (s, 3H, —NCH$_3$), 3.38 (s, 2H, CH$_2$CONH—), 7.66 (dd, J=8.55 Hz, 2.02 Hz, 1H, Ar—$\underline{H}$), 7.92 (d, J=1.97 Hz, 1H, Ar—$\underline{H}$), 8.13 (d, J=8.52 Hz, 1H, Ar—$\underline{H}$), 11.99 (s, 1H, —CON$\underline{H}$CO—); IR (KBr, cm$^{-1}$): 3350 (NH), 1750 (CO), 1730 (CO), 1660 (CO); MS (m/e): 293 (M+H)$^+$; M.P. 213°-214° C.

Anal. Calc'd: C, 53.35; H, 3.10; N, 9.57, Found: C, 53.43; H, 3.09; N, 9.38.

2-Methylspiro[isoquinoline-4(1H),3'-pyrrolidine]-1,2',3,5'(2H)-tetrone $^1$H NMR (DMSO-d$_6$, 400 MHz): δ3.24 (s, 3H, —N—CH$_3$), 3.43 (q, J=18.38 Hz, 2H, —C$\underline{H_2}$CONH—), 7.58-7.64 (m, 2H, Ar—$\underline{H}$), 7.74 (dt, J=7.64 Hz, 1.2 Hz, 1.2 Hz, 1H, Ar—$\underline{H}$), 8.15 (dd, J=7.72 Hz, 0.94 Hz, 1H, Ar—$\underline{H}$), 12.0 (2, 1H, —CON$\underline{H}$CO—), IR (KBr, cm$^{-1}$): 3340 (NH), 1720 (CO), 1660(CO); MS (m/e): 258 (M+); M.P. 224°-225° C.

Anal. Calc'd: C, 60.47; H, 3.90; N, 10.85, Found: C, 60.27; H, 4.03; N, 10.82.

I claim:
1. The compound of formula V

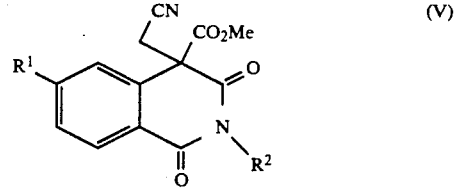

wherein:
R$^1$ is hydrogen or halogen and R$^2$ is dihalogen substituted benzyl or methyl.

* * * * *